United States Patent
Zimmerman et al.

(12)

(10) Patent No.: US 8,091,423 B2
(45) Date of Patent: Jan. 10, 2012

(54) WELD VERIFICATION SYSTEM AND METHOD

(75) Inventors: Kurt M. Zimmerman, North Tonawanda, NY (US); Gregory L. Bolis, Akron, NY (US)

(73) Assignee: American Axle & Manufacturing, Inc., Detroit, MI (US)

( * ) Notice: Subject to any disclaimer, the term of this patent is extended or adjusted under 35 U.S.C. 154(b) by 374 days.

(21) Appl. No.: 12/423,225

(22) Filed: Apr. 14, 2009

(65) Prior Publication Data

US 2009/0255341 A1   Oct. 15, 2009

Related U.S. Application Data

(60) Provisional application No. 61/045,042, filed on Apr. 15, 2008.

(51) Int. Cl.
*G01M 7/00* (2006.01)
(52) U.S. Cl. .......................................... 73/588
(58) Field of Classification Search .................. 73/588, 73/644, 620, 597, 598; 288/104; 702/39
See application file for complete search history.

(56) References Cited

U.S. PATENT DOCUMENTS

| | | | |
|---|---|---|---|
| 3,791,199 A | 2/1974 | Toth et al. | |
| 3,868,847 A | 3/1975 | Gunkel | |
| 3,888,114 A | 6/1975 | Adams, Jr. et al. | |
| 4,208,917 A * | 6/1980 | Aoyama et al. | 73/644 |
| 4,351,190 A | 9/1982 | Rehme et al. | |
| 4,821,575 A | 4/1989 | Fujikake et al. | |
| 5,007,291 A | 4/1991 | Walters et al. | |
| 5,537,875 A * | 7/1996 | Viehmann et al. | 73/588 |
| 5,583,292 A | 12/1996 | Karbach et al. | |
| 5,677,490 A | 10/1997 | Gunther et al. | |
| 6,425,870 B1 | 7/2002 | Flesch | |
| 6,578,422 B2 | 6/2003 | Lam et al. | |
| 6,733,457 B2 | 5/2004 | Flesch et al. | |
| 6,896,171 B2 | 5/2005 | Den Boer et al. | |
| 6,948,369 B2 * | 9/2005 | Fleming et al. | 73/588 |
| 7,021,143 B2 | 4/2006 | Dasch | |
| 7,150,193 B2 | 12/2006 | Lorraine et al. | |
| 7,204,147 B2 | 4/2007 | Fujimoto et al. | |
| 7,263,887 B2 | 9/2007 | Sfeir et al. | |
| 7,516,022 B2 * | 4/2009 | Lee et al. | 702/39 |
| 7,789,286 B2 * | 9/2010 | Maev et al. | 228/104 |
| 2004/0245315 A1 | 12/2004 | Maev et al. | |
| 2005/0230360 A1 | 10/2005 | Maev et al. | |
| 2009/0078742 A1 * | 3/2009 | Pasquali et al. | 228/103 |

FOREIGN PATENT DOCUMENTS

| | | |
|---|---|---|
| DE | 019713370 A1 | 10/1998 |
| JP | 57-114852 | 7/1982 |
| JP | 2000197631 A | 7/2000 |
| JP | 2002031624 A | 1/2002 |
| WO | WO 2007/006904 | 1/2007 |

* cited by examiner

*Primary Examiner* — Jewel V Thompson
(74) *Attorney, Agent, or Firm* — Harness, Dickey & Pierce, P.L.C.

(57) ABSTRACT

An inspection method and system that locates a probe proximate a region of a shaft that is welded to a slug that secures the shaft to a housing. An acoustical wavefront may be emitted from the probe into the shaft toward the slug, and a reflection of the acoustical wavefront may be received with the probe. Whether the reflection occurred at an interface between the shaft and the slug or at a distal end of the slug is determined based on a time that the reflection is received by the probe.

20 Claims, 4 Drawing Sheets

WELD VERIFICATION SYSTEM AND METHOD

This application claims the benefit of U.S. Provisional Patent Application Ser. No. 61/045,042 filed Apr. 15, 2008 entitled "Weld Verification System And Method", the disclosure of which is incorporated by reference as if fully set forth in detail herein.

BACKGROUND

The present disclosure relates to a weld verification system and a related method for inspecting slug welds.

The statements in this section merely provide background information related to the present disclosure and may not constitute prior art.

Slugs may be used to couple a shaft to a housing. In this regard, slugs that pass through the housing may be resistance welded to the shaft. For quality assurance purposes, these resistance welds may be inspected periodically to ensure that housing and shaft are securely coupled. To inspect the welds, destructive methods may be used where the shaft is torqued relative to the housing to determine the amount of force required to break the resistance weld. Because such a method destroys the housing/shaft assembly, however, the assembly may not be placed back into use and, therefore, this method is not cost-effective.

SUMMARY

In one form, the teachings of the present disclosure provide an inspection method that locates a probe proximate a region of a shaft that is welded to a slug that secures the shaft to a housing. An acoustical wavefront may be emitted from the probe into the shaft toward the slug, and a reflection of the acoustical wavefront may be received with the probe. Whether the reflection occurred at an interface between the shaft and the slug or at a distal end of the slug is determined based on a time that the reflection is received by the probe.

In another form, the teachings of the present disclosure provide an inspection system for inspecting a weld at an interface between a slug and a hollow shaft. The system includes a probe that emits an acoustical wavefront into the shaft toward the slug and receives a reflection of the acoustical wavefront. An acquisition unit transmits a signal to the probe to emit the acoustical wavefront and converts a return signal received from the probe after the reflection is received by the probe into an image.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
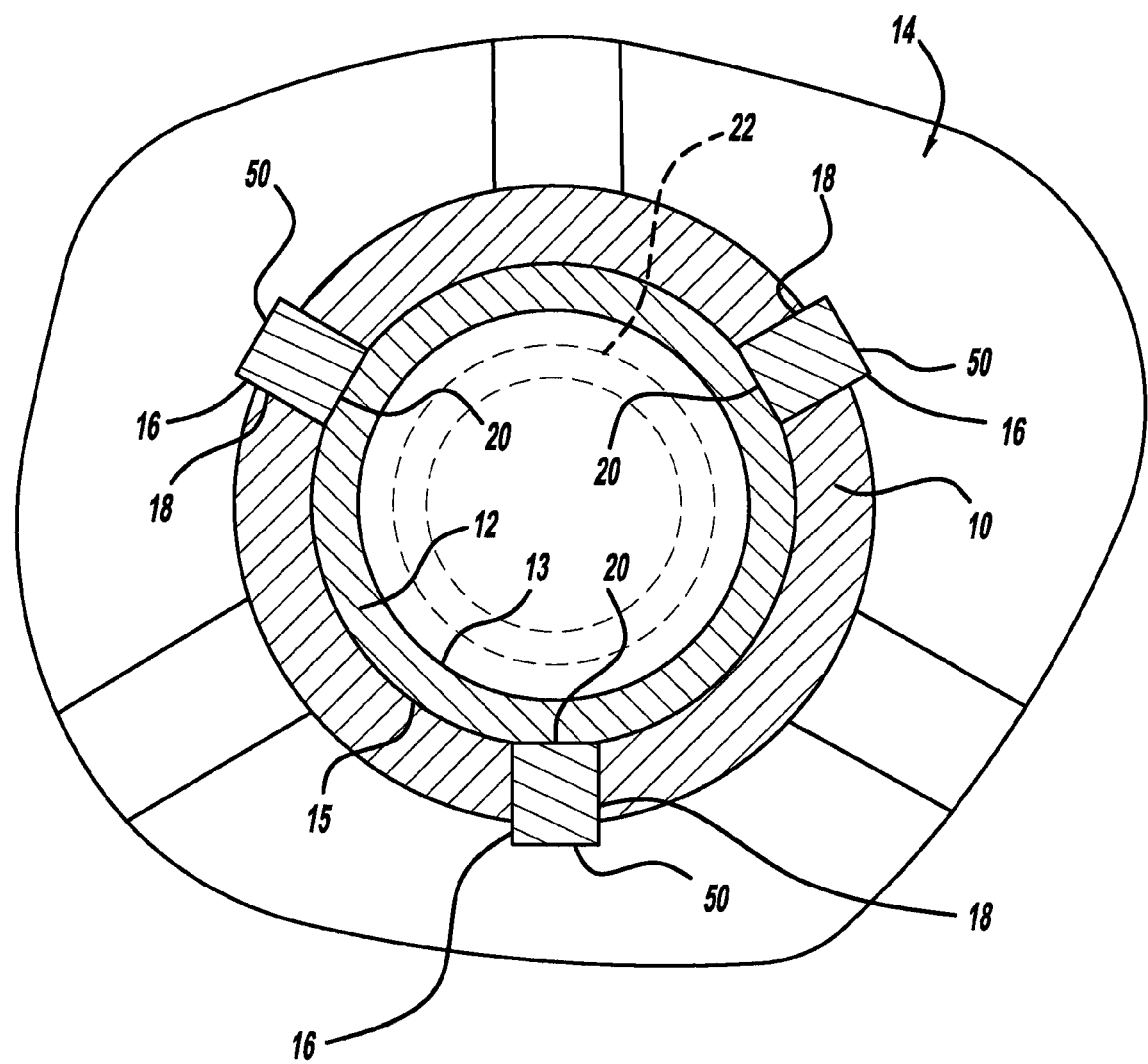
FIG. 1 is a cross-sectional view of an exemplary assembly in which a plurality of slugs are employed to couple a housing to a shaft.

The following description is merely exemplary in nature and is not intended to limit the present disclosure, application, or uses. It should be understood that throughout the drawings, corresponding reference numerals indicate like or corresponding parts and features.

With reference to FIG. 1, an exemplary housing 10 is secured to a shaft 12 to form a shaft/housing assembly 14 via slugs 16. Housing 10 may include through-holes 18 that receive slugs 16 and, to secure housing 10 to shaft 12, and resistance welding can be employed to form a weld at an interface between shaft 12 and slugs 16. In this regard, slug 16 can be placed into through hole 18 and abutted against shaft 12, a pair of electrodes (not shown) can be electrically coupled to slug 16 and shaft 12 (e.g., to an inner surface 12 of shaft 12) and electric power can be passed through the electrodes to couple slug 16 to shaft 12. Passing a current between slug 16 and shaft 12 in this manner results in the formation of a resistance weld at the interface 20 between slug 16 and shaft 12, which axially and non-rotatably secures shaft 12 to housing 10.

The integrity of these resistance welds may be checked periodically. Any type of ultrasonic testing, which is a form of non-destructive testing, may be employed for this task. In this particular example provided, however, phased array ultrasonic testing is employed. Phased array testing is a specialized type of ultrasonic testing that uses multi-element array probes and software to steer high frequency acoustic beams through the slug 16 and shaft 12 and map returning echoes, producing detailed images of the resistance weld between the slug 16 and the shaft 12.

Phased array testing offer significant technical advantages over conventional ultrasonic testing such as the use of electronic scanning, beam forming, beam steering, and electronic focusing. Electronic scanning permits very rapid coverage of the components, typically an order of magnitude faster than a single-probe mechanical system. Beam forming permits selected beam angles to be optimized ultrasonically by orienting them perpendicularly to the predicted defects (e.g., the lack of fusion in a weld).

The dominant features of phased arrays include speed, flexibility, inspection angles, small footprint, and imaging. Imaging, in particular, is useful for weld inspections, particularly for defect sizing. Scanning with phased arrays is much faster than single-probe conventional mechanical systems and, at the same time, provides better coverage. Setups may be changed in a few minutes, and typically more component-dimension flexibility is available. A wide variety of inspection angles may be used, depending on the requirements and the array. Small matrix arrays may give significantly more flexibility than conventional probes for inspecting restricted areas. In addition, showing a true depth image of defects is much easier to interpret than a waveform. The data may then be saved and redisplayed as required.

Conventional ultrasonic transducers for non-destructive testing (NDT) commonly consist of either a single active element that both generates and receives high frequency sound waves, or two paired elements, one for transmitting and one for receiving. Phased array probes, in contrast, typically consist of a transducer assembly having sixteen to as many as two hundred fifty-six small individual elements that may each be pulsed separately. These may be arranged in a strip (linear array), a ring (annular array), a circular matrix (circular array), or a more complex shape. As is the case with conventional transducers, phased array probes may be designed for direct contact use, as part of an angle beam assembly with a wedge, or for immersion use with sound coupling through a fluid (e.g., water) path. Transducer frequencies are most commonly in the range from 2 MHz to 10 MHz. A phased array system, such as that which is shown in FIG. 2, can also include a sophisticated computer-based instrument or acquisition unit that is capable of driving the multi-element probe, receiving and digitizing the returning echoes, and plotting that echo information in various standard formats.

Figure 2:
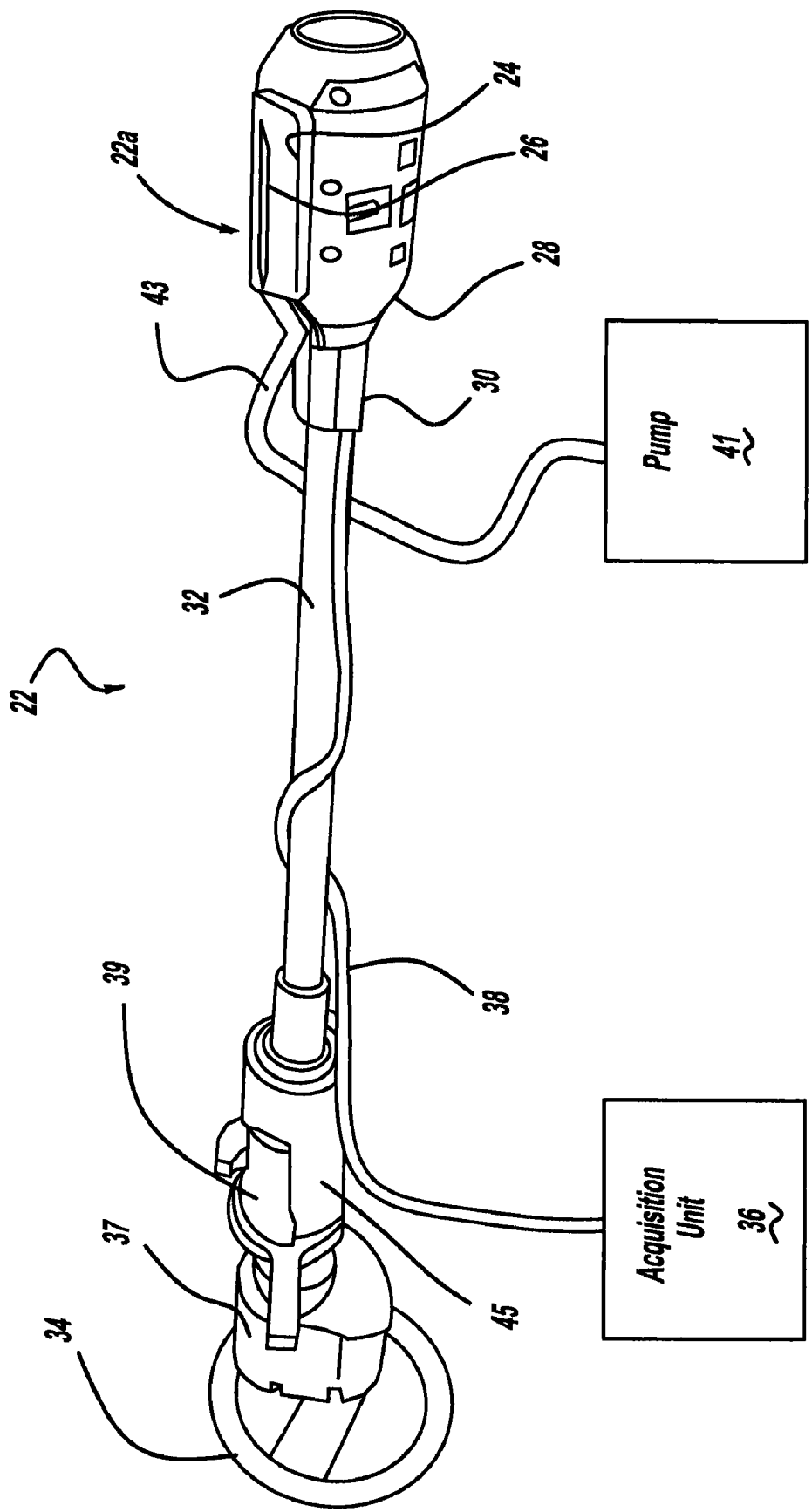
FIG. 2 is a perspective view of a inspection device constructed in accordance with the teachings of the present disclosure.

With reference to FIG. 2, a weld inspection system constructed in accordance with the teachings of the present disclosure is generally indicated by reference numeral 22. The weld inspection system 22 can include a phased array system 22a having a linear array 24. The linear array 24 can be composed of a plurality of elements 26, such as sixty-four individual elements. Elements 26 may be piezoelectric elements formed of quartz or composite piezoelectric elements. Although piezoelectric elements are utilized in the linear phased array 24, it should be understood that any other element or device that is capable of emitting an acoustic wave may be used.

The weld inspection system 22 can include a probe 28, a connection shaft 32 and a handle 34. The probe 28 can be mounted to a distal end 30 of the connection shaft 32 and is sized to be received within the shaft 12 (FIG. 1). Elements 26 of linear phased array 24 can be mounted to the probe 28. Handle 34 can be coupled to an opposite (proximal) end of the connection shaft 32 and is configured to transfer rotary motion from an operator (e.g., an operator's hand) to the connection shaft 32 to permit the probe 28 to be rotated within the shaft 12 (FIG. 1). Probe 28 can be coupled to an acquisition unit 36 in any desired manner, such as via a coaxial cable 38. Acquisition unit 36 may be a portable unit that is not coupled to the shaft or, alternatively, may be mounted to connection shaft 32.

Weld inspection device 22 can also include an encoder 37 that can be employed to correlate a rotational position of probe 28 to shaft 12 (FIG. 1) and/or slug 16 (FIG. 1), as well as a rotational lock 39, such as a collet, that can facilitate the mounting and non-rotatable securing of the encoder 37 to shaft 12 (FIG. 1). For example, rotational lock 39 may be a holding device that exerts a clamping force on shaft 12 (FIG. 1) to secure weld inspection device 22 to shaft 12 (FIG. 1) and, accordingly, when handle 34 is rotated, only connection shaft 32 and probe 28 will rotate relative to shaft 12 (FIG. 1) and slug 16 (FIG. 1), which is monitored by encoder 37.

Weld inspection device 22 can also include a pump 41 and conduit system 43 that is configured to provide an ultrasonic couplant between shaft 12 (FIG. 1) and probe 28 during inspection of a slug weld. The ultrasonic couplant may also act as a lubricant that assists in lubricating the rotational motion between probe 28 and shaft 12 (FIG. 1).

Figure 3A:
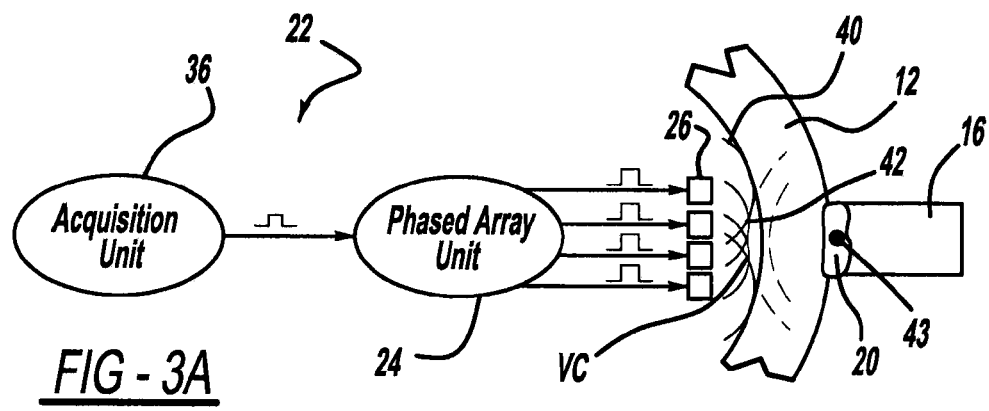
FIGS. 3A and 3B are schematic illustrations of the inspection device of FIG. 2 sending and receiving, respectively, ultrasonic waves into the exemplary assembly of FIG. 1.

FIG. 3A schematically illustrates the emisson of an acoustic wavefront from the prove elements 26. Acquisition unit 36 can provide a trigger signal to the phased array unit 24, which can responsively generate a plurality of signal pulses that can be received by the elements 26 of the linear array 24. The elements 26 can responsively generate individual acoustic waves 40. The acoustic waves 40 emitted by the elements 26 may combine (constructively and/or destructively) to form a single wavefront 42 that travels through the ultrasonic couplant C and into the material to be inspected, which can include the weld slug 16.

The wavefront 42 can travel through the material to be inspected at a velocity that, based on a given temperature and pressure, will be constant in a homogeneous elastic material such as, for example, steel, cast iron or aluminum. Accordingly, when the slugs 16 and shaft 12 are resistance welded together or fused, the wavefront 42 should travel through the interface 20 between the slug 16 and shaft 12 at a constant velocity.

Phased array system 22a can be configured to sweep the acoustic wavefront 42 through a range of refracted angles, along a linear path, or dynamically focus at a number of different depths. This variability can increase both the flexibility and capability of inspection setups. Phased array system 22a can utilize the wave physics principle of phasing to vary the time between a series of outgoing ultrasonic pulses in such a way that the individual waves 40 generated by each element 26 in the array 24 combine with each other to add or cancel energy in predictable ways that effectively steer and shape the acoustic wavefront 42.

This may be implemented, for example, by pulsing the individual elements 26 at slightly different times. For example, the elements 26 can be pulsed in groups of four to thirty-two in order to improve effective sensitivity, which can reduce beam spreading and enable sharper focusing. Software in the acquisition unit 36 may establish specific delay times for actuating each group of elements 26 in order to generate the desired wavefront 42 shape, taking into account probe 28 characteristics and geometry and acoustical properties of the test material. The programmed pulsing sequence selected by the operating software of the acquisition unit 36 then launches a number of individual waves 40 into the test material.

The acoustic wavefront 42 may be dynamically steered through various angles, focal distances, and focal spot sizes in such a way that a single probe assembly is capable of examining the test material across a range of different perspectives. This beam steering happens very quickly, so that a scan from multiple angles or with multiple focal depths may be performed in a small fraction of a second.

Figure 3B:
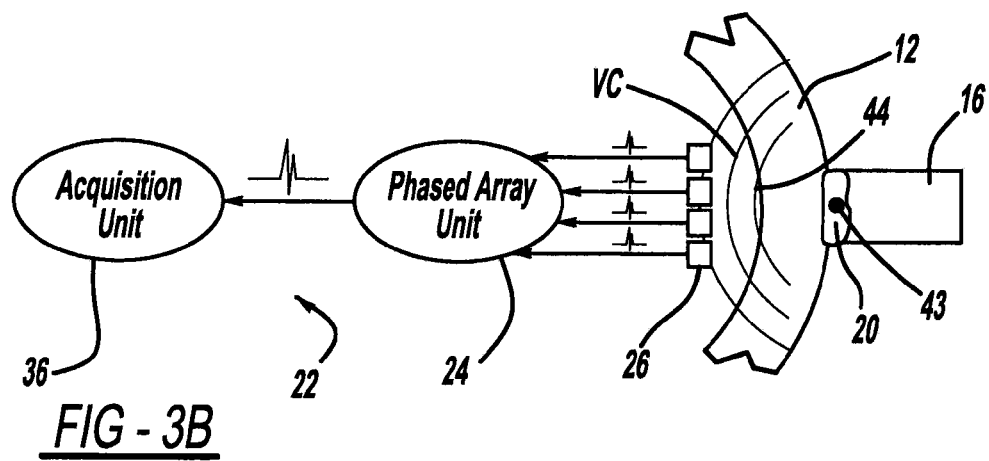

With reference to FIG. 3B, if a flaw or defect 43 is present in the interface 20, a reflection or echo 44 of the wavefront 42 (FIG. 3A) will can be generated and can travel back toward the elements 26 of the linear phased array 24. The echo 44 can be received by the elements 26, which can convert the acoustic energy into electrical energy and send the electrical energy (i.e., the electric echo signal) to the phased array unit 24 and/or the acquisition unit 36.

Unlike a conventional single element transducer, which will effectively merge the effects of all beam components that strike its area, the phased array system 22a can be configured to spatially sort the returning wavefront 44 according to the arrival time and amplitude at each element 26. Each echo 44 represents the reflection from a particular angular component of the beam, a particular point along a linear path, and/or a reflection from a particular focal depth. The echo information can then be displayed in any of several formats.

In this regard, in flaw detection applications, the ultrasonic test data will be based on time and amplitude information derived from processed RF waveforms. These waveforms and the information extracted from them will commonly be presented in one or more of four formats: A-scans, B-scans, C-scans, or S-scans. As will be appreciated by those of skill in the art, an A-scan is a simple RF waveform presentation showing the time and amplitude of an ultrasonic signal, as commonly provided by conventional ultrasonic flaw detectors. An A-scan waveform represents the reflections 44 from one sound beam position in the test piece. Phased array system 22 may display A-scan waveforms for reference; however, in most cases, this data will be supplemented by B-scans, C-scans, or S-scans. These standard imaging formats aid the operator in visualizing the type and position of flaws in a test piece.

A B-scan is an image showing a cross-sectional profile through one vertical slice of the test piece, showing the depth of reflectors with respect to their linear position. B-scan imaging requires that the sound beam be scanned along the selected axis of the test piece, either mechanically or electronically, while storing relevant data.

A C-scan is a two dimensional presentation of data displayed as a top or planar view of a test piece, similar in its graphic perspective to an x-ray image, where color represents the gated signal amplitude at each point in the test piece mapped to its x-y position. With conventional instruments, the single-element transducer must be moved in an x-y raster scan pattern over the test piece. With phased array systems, the probe is typically moved physically along one axis while the beam electronically scans along the other. Encoders will normally be used whenever precise geometrical correspondence of the scan image to the part must be maintained, although unencoded manual scans may also provide useful information in many cases.

Lastly, an S-scan (sectorial scan) image represents a two-dimensional cross-sectional view derived from a series of A-scans that have been plotted with respect to time delay and refracted angle. The horizontal axis corresponds to test piece width, and the vertical axis to depth. This is the most common format for medical sonograms as well as for industrial phased array images. The acoustic wavefront 42 sweeps through a series of angles to generate an approximately cone-shaped cross-sectional image.

As briefly stated above, the benefits of phased array technology over conventional ultrasonic testing arise from its ability to use multiple elements 26 to steer, focus and scan beams with a single transducer assembly. Beam steering may be used for mapping components at appropriate angles, which may simplify the inspection of components with complex geometries. The small footprint of the transducer and the ability to sweep the beam without moving the probe also aids inspection of such components in situations where there is limited access for mechanical scanning. Beam steering is also beneficial for weld inspection due to the ability to test welds with multiple angles from a single probe, which greatly increases the probability of detection of a defect or flaw.

Electronic focusing permits optimizing the beam shape and size at the expected defect location, thus further optimizing probability of detection. The ability to focus at multiple depths also improves the ability for sizing critical defects for volumetric inspections. Focusing may also improve signal-to-noise ratio in challenging applications, and electronic scanning across many groups of elements allows for C-scan images to be produced very rapidly.

Figure 4:
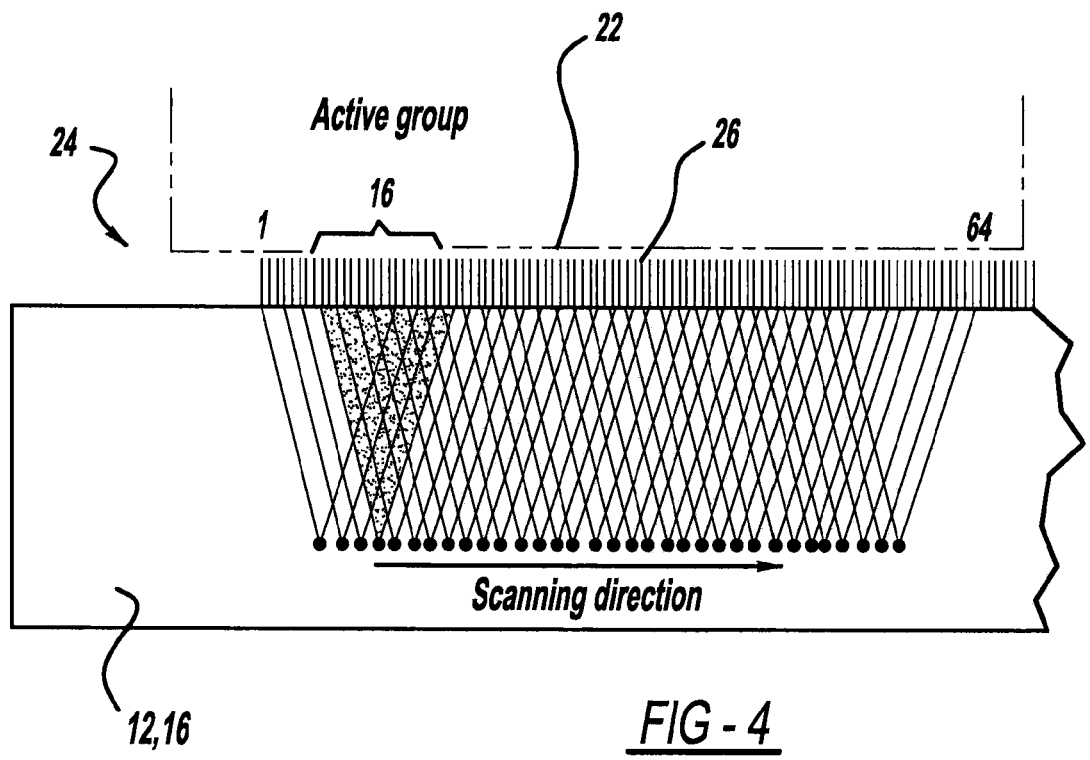
FIG. 4 is a schematic illustration of the multiplexing a plurality of elements of a linear phased array.

The elements 26 of the linear phased array 24 are all individually wired, pulsed, and time-shifted. As shown in FIG. 4, elements 26 are normally pulsed in groups that range in number from four to thirty-two (out of sixty-four) that enables the wavefront 42 to be steered and focused at the interface 20 as desired. The acquisition and analysis software calculates the time delays for a setup from operator input on inspection angle, focal distance, scan pattern, etc. Time-delay circuits should be near 2-nanosecond accuracy to provide the phasing accuracy required. Each element 26 generates a wave 40 when pulsed and the phased array instrumentation 24 pulses the individual channels with time delays as specified to form a pre-calculated wavefront 42. For receiving, the instrumentation 24 effectively performs the reverse. For example, the instrumentation 24 receives signals with pre-calculated time delays, sums the time-shifted signal, and then displays it. As phased arrays offer considerable application flexibility, software versatility is highly desirable, and the application software needs to be powerful to manage the acquisition of UT (ultrasonic testing) signals.

Referring to FIGS. 3A-5, the weld inspection method according to the present teachings will now be described. The linear phased array 24 is comprised of sixty-four elements 26 that may generate a plurality of waves 40 that destructively and constructively combine to form a single acoustic wavefront 42 that penetrates an inner wall 13 of the shaft 12, through the interface 20 between the shaft 12 and the slug 16, and through the slug 16. Once the wavefront 42 reaches the distal end of the slug 16 (i.e., an end of the slug 16 located away from the interface 20 between the slug 16 and the shaft 12), the wavefront 42 is reflected and returns to the linear phased array 24.

As stated above, both the shaft 12 and slug 16 are formed of the same material which may be, for example, steel. Accordingly, when the shaft 12 and slug 16 are welded together, the acoustic wavefront 42 should travel through both the shaft 12 and slug 16 as if the shaft 12 and slug 14 were a unitary body and reflect back to the linear phased array 24 once the acoustic wavefront 42 reaches the distal end 50 of the slug 16.

Shafts 12 used in the housing/shaft assembly 14 generally include a predetermined thickness that is reproducible during production of the shafts 12 due to strict manufacturing tolerances. The predetermined thickness may be used to calculate the time needed for the acoustic wavefront 42 to reach the interface 20 between the shaft 12 and the slug 16. In contrast to the predetermined thickness of the shafts 12, the slugs 16 used to secure the housing 10 to the shaft 12 have relatively large manufacturing tolerances, or a length of the slug 16 may be formed to have a variety of lengths that may vary from slug to slug.

Figure 5:
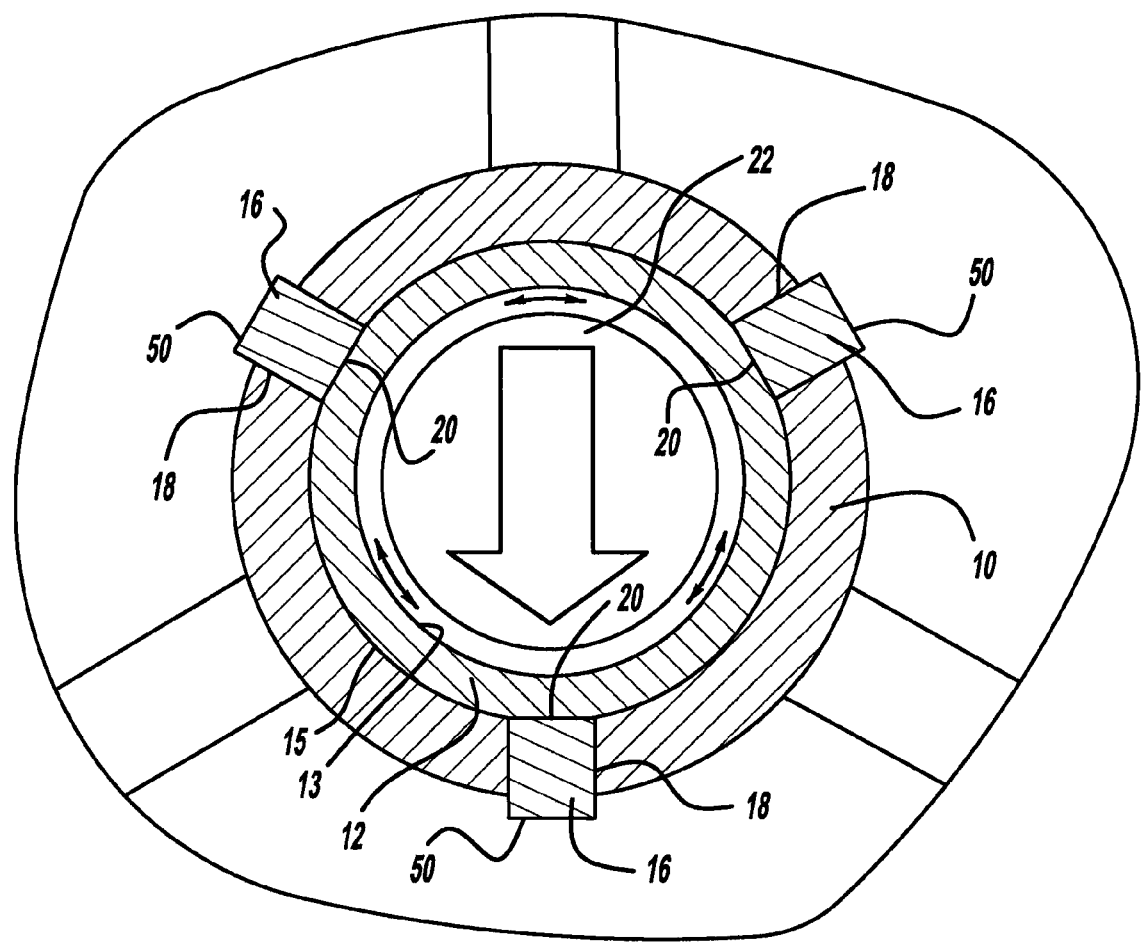
FIG. 5 is a cross-sectional view similar to that of FIG. 1 but illustrating the inspection device of FIG. 2 inserted thereto for inspecting the interface between a slug and a shaft.

With additional reference to FIG. 5, it will be appreciated that as the shaft 12 has a relatively constant wall thickness, the placement of the linear phased array 24 within the shaft 12 and emitting the acoustic wavefront 42 in a direction toward the slug 16 results in a relatively constant length of time that is needed for the wavefront 42 to reach the interface 20. Consequently, the amount of time needed to generate the echo 44 may be used as a reference point for determining whether a defect or flaw is present in the weld located at the interface 20 between the slug 16 and the shaft 12.

More specifically, utilizing the amount of time it should take for the acoustic wavefront 42 to travel through the thickness of the shaft 12 and reflect back to the elements 26, it may be determined whether the acoustic wavefront 42 has traveled through the interface 20 and been reflected at the distal end 50 of the slug 16. If the reflected wavefront 44 is received after a time that is at least twice as great as the amount of time for the acoustic wavefront 42 to initially reach the interface 20, the weld at the interface 20 between the shaft 12 and slug 16 should be satisfactory. In contrast, if the reflected wavefront 44 is received in an amount of time that is less than twice the amount of time that the wavefront 42 should take to reach the interface 20, then a defect or flaw 43 may be present in the weld at the interface 20.

To ensure that the entire weld at the interface 20 between the slug 16 and shaft 12 is inspected, the acoustic wavefront 42 may be swept through a range of refracted angles, along a linear path, or dynamically focused at a number of different depths by varying the timing at which the elements 26 of the array 24 are actuated. Alternatively, the linear phased array 24 may be manually swept or rotated (i.e., "rastered") using the handle 34 of the device 22 to ensure that the entire region proximate the interface 20 between the slug 16 and shaft 12 is inspected. The manual rotation of the linear phased array 24 is tracked by encoder 37 to ensure that the entire region proximate the interface 20 is inspected. Encoder 37 may track rotation in any direction to ensure that a full 360 degrees of shaft 12 is inspected. After inspection data is received for inspections that occur when probe 28 is rotated in one direction, probe 28 may be rotated in the opposite direction and data received from those inspections may be compared to the prior data received. In this manner, the interface 20 may be fully and reliably inspected. Regardless, it should be understood that to satisfactorily make a determination whether the weld is robust enough to pass inspection, the entire weld at the interface 20 is inspected.

If a defect or flaw 43 is determined to be present in the weld at the interface 20 between the slug 16 and the shaft 12, a decision may then be made whether the housing/shaft assembly 14 is acceptably coupled depending on the size of the defect or flaw 43. In this regard, the reflected wavefront 44 or echo detected by the elements 26 the linear-phased array 24 may be converted into an electric signal that is subsequently sent to the acquisition unit 36. The acquisition unit 36 may then display an image (i.e., an A-scan, B-scan, C-scan, or S-scan) that provides the operator with a visual representation of the defect 43 present at the interface 20 between the slug 16 and the shaft 12.

Because the linear-phased array 24 is coupled to a connection shaft 32, the user or operator may rotate the linear-phased array 24 to sweep or raster an entire width of the slug 16. Moreover, because the linear phased array 24 is rotatable, the operator may merely rotate the linear-phased array 24 to the next location of the slug 16 that couples the housing 10 to the shaft 12. Again, this simplifies and quickens the rate at which the interface 20 is inspected. Moreover, since the weld is not destroyed to test the robustness of the weld, if the assembly passes inspection, it may be reinserted into the assembly line and no reduction or loss is experienced.

What is claimed is:

1. An inspection method comprising:
    locating a probe proximate a region of a shaft that is welded to a slug that secures said shaft to a housing;
    emitting an acoustical wavefront from said probe into said shaft toward said slug;
    receiving a reflection of said acoustical wavefront with said probe; and
    determining whether said acoustical wavefront was reflected at a point beyond an interface between said shaft and said slug.

2. The inspection method of claim 1, wherein said probe is a phased array.

3. The inspection method of claim 2, wherein said phased array is a linear phased array.

4. The inspection method of claim 2, wherein said phased array includes a plurality of elements that emit a plurality of acoustical waves that combine to form said wavefront.

5. The inspection method of claim 1, wherein said probe is located within said shaft proximate the region of said shaft that is welded to said slug.

6. The inspection method of claim 1, wherein said shaft includes a predetermined thickness and said slug has a variable length.

7. The inspection method of claim 6, wherein said step of determining whether said reflection occurred at said interface between said shaft and said slug or at said distal end of said slug based on said time that said reflection is received by said probe utilizes said predetermined thickness of said shaft.

8. The inspection method of claim 1, further comprising a step of determining whether a defect is present in a weld located at said interface between said shaft and said slug if said reflection is occurs at said interface.

9. The inspection method of claim 1, wherein said step of emitting an acoustical wavefront from said probe into said shaft toward said slug includes focusing said acoustical wavefront at said interface.

10. The inspection method of claim 1, wherein said step of emitting an acoustical wavefront from said probe into said shaft toward said slug includes steering said acoustical wavefront toward said interface.

11. An inspection system for inspecting a weld at an interface between a slug and a hollow shaft comprising:
    a probe that emits an acoustical wavefront into the shaft toward the slug and receives a reflection of said acoustical wavefront;
    an acquisition unit that transmits a signal to said probe to emit said acoustical wavefront and converts a return signal received from said probe after said reflection is received by said probe into an image;
    an encoder for monitoring rotational movement of said probe relative to the shaft and the slug; and
    a pump for feeding an ultrasonic couplant between said probe and the shaft.

12. The inspection system of claim 11, wherein said probe is a phased array.

13. The inspection system of claim 12, wherein said phased array is a linear phased array.

14. The inspection system of claim 12, wherein said phased array includes a plurality of elements that emit a plurality of acoustical waves that combine to form said wavefront.

15. The inspection system of claim 11, wherein said probe is located within the shaft proximate a region of the shaft that is welded to the slug.

16. The inspection system of claim 11, wherein said shaft includes a predetermined thickness and said slug has a variable length.

17. The inspection system of claim 16, wherein said acquisition unit is adapted to determine whether said reflection occurred at the interface between the shaft and the slug or at a distal end of the slug based on a time that said reflection is received by said probe based on predetermined thickness of said shaft.

18. The inspection system of claim 11, wherein said acquisition unit is adapted to determine whether a defect is present in a weld located at the interface between the shaft and the slug if said reflection occurs at the interface.

19. The inspection system of claim 11, wherein said signal emitted by said acquisition unit to said probe causes a plurality of elements of said probe to emit acoustical waves that combine to form said acoustical wavefront that is steered and focused at the interface.

20. An inspection method, comprising:
    locating a probe having a linear phased array including a plurality of elements that emit a plurality of acoustical waves that combine to form a single acoustic wavefront proximate region of a shaft having a predetermined thickness that is welded to a plurality of slugs having a variable length that secures said shaft to a housing;
    emitting said acoustical wavefront from said probe into said shaft toward a first slug of said plurality of slugs;

focusing said acoustical wavefront at an interface between said shaft and said first slug;
steering said acoustical wavefront toward said interface between said shaft and said first slug;
receiving a reflection of said acoustical wavefront with said probe;
determining whether said acoustical wavefront was reflected at a point beyond said interface between said shaft and said first slug;
determining whether a defect is present in a weld located at said interface between said shaft and said first slug if said reflection occurs at said interface;
rotating said probe in said shaft to inspect remaining slugs of the plurality of slugs; and
monitoring rotation of said probe with an encoder.

* * * * *